United States Patent [19]

Thomas et al.

[11] Patent Number: 5,558,987

[45] Date of Patent: Sep. 24, 1996

[54] BLOOD LEVELS OF CCK PEPTIDES RELATIVE TO PANIC DISORDER TREATMENT

[75] Inventors: Thomas N. Thomas, Palm Harbor; David V. Sheehan; Janet D. Talbot, both of Lutz, all of Fla.

[73] Assignee: University of South Florida, Tampa, Fla.

[21] Appl. No.: 341,846

[22] Filed: Nov. 18, 1994

Related U.S. Application Data

[63] Continuation of Ser. No. 168,913, Dec. 16, 1993, abandoned, which is a continuation of Ser. No. 914,849, Jul. 15, 1992, abandoned.

[51] Int. Cl.⁶ .................. C12Q 1/00; C12Q 1/37; G01N 31/00; A61K 38/00
[52] U.S. Cl. .................. 435/4; 435/23; 435/24; 436/16; 436/86; 436/74; 436/63; 514/2; 530/300; 530/302; 530/314; 530/417; 210/656
[58] Field of Search .................. 435/130, 4, 23, 435/24; 436/86, 16, 74, 63; 530/324, 302, 417, 300, 314; 210/656

[56] References Cited

U.S. PATENT DOCUMENTS

| | | | |
|---|---|---|---|
| 4,508,726 | 4/1985 | Coleman | 514/220 |
| 4,634,703 | 1/1987 | Kurtz et al. | 514/252 |
| 4,794,103 | 12/1988 | Bertolini | 514/12 |
| 5,166,151 | 11/1992 | Freidinger et al. | 514/215 |

FOREIGN PATENT DOCUMENTS 0486271   5/1992   European Pat. Off. .

OTHER PUBLICATIONS

Chem Abstract, vol. 111(13:108885 S (Robinson et al).
Woodruff et al, "Annu. Rev. Pharm. Toxicol.", vol. 31, pp. 469–501, (1991).
Bradwejn et al, "Arch Gen Psy", pp. 603–610, (1991).
Savter et al; J. Chromatography, 297:215–223 (1984).
Bibb et al; "Behav. Res. Ther.", 24:49–58; Alcohol Use & Abuse Among Diagnosed Agoraphobics; (1986).
Passaro et al; "Brain Research"; 241:335–340; Rapid Appearance of Intraventricularly Administered Neuropeptides in Peripheral Circulation; (1982).
Chen et al, (Abstract), "Drug Metab Dispos", 20(3),(1992) p. 390.
Klerman, G. L., Weissman, M. M., Ouellette, R., Johnson, J. and Greenwald, S. *JAMA* 256, 742–746 (1991).
White, P. D. & Jones, T. D. *New Eng. Am. Heart J.* 3, 302–318 (1928).
Wood, P. *Br. Med. J.* 1, 767–772, 805–822, 845–851 (1941).
Wheeler, E. O., White, P. D., Reed, E. W., & Cohen, M. E. *JAMA* 142, 878–889 (1950).
Marks, I. & Lader, M. *J. Nerv. Ment. Dis.* 156, 3–18 (1973).
Robins, L. N. Helzer, J. E., Weissman, M. M. et al. *Arch. Gen. Psychiatr.* 41, 949–958 (1984).
Sheehan, D. V., Sheehan, K. E., & Minichello, W. E. *Compr. Psychiatr.* 22, 544–553 (1981).
Torgersen, S. *Arch. Gen. Psychiatr.*40, 1085–1089 (1983).

(List continued on next page.)

Primary Examiner—John Kight
Assistant Examiner—Louise N. Leary
Attorney, Agent, or Firm—Kohn & Associates

[57] ABSTRACT

A method of treating a patient having a panic disorder, the patient having an elevated CCK peptide plasma level, by lowering the plasma CCK peptide level of the patient. A further method provides a diagnosis of panic disorder in a patient by detecting if that patient's plasma contains elevated CCK peptide levels. A further method determines the efficacy of the drug for the treatment of panic disorder by detecting the ability of the drug to lower elevated CCK peptide levels in a model for panic disorder. Additionally, a method of dosing a patient having elevated CCK peptide levels with an antipanic disorder drug is characterized by administering the drug to a patient and monitoring the lowering of the elevated plasma CCK peptide levels of the patient.

9 Claims, 4 Drawing Sheets

OTHER PUBLICATIONS

McNair, D. M. Kahn, R. J. in *Anxiety: New Research and Changing Concepts* (eds. Klein, D. F. & Rabkin, J.) 69–79 (Raven, New York 1981).

Crowe, R. R., Pauls, D. L. Slymen, D. J., Noyes, R. *Am. J. Hum. Genetics* 32, 639–644 (1980).

Pauls, D. L., Bocher, K. D., Crowe, R. R. et al. *Am. J. Hum. Genet.* 32, 639–644 (1980).

Crowe, R. R., Noyes, R., Wilson, A. F. et al. *Arch. Gen. Psychiatr.* 44, 933–937 (1987).

Liberthson, R., Sheehan, D. V., King, M. E. et al. *Am. J. Psychiatr.* 143, 511–515 (1986).

Noyes, R., Clancy, J., Hoenk, P. R., & Slymen, D. J. *Comp. Psychiatr.* 19, 407–413 (1978).

Coryell, W., Noyes, R., & Clancy, J. *Arch. Gen. Psychiatr.* 39, 701–703 (1982).

Bradwejn, J., Koszycki, B. & Shriqui, C. *Arch. Gen. Psychiatr.* 48, 603–610 (1991).

Bradwejn, J. & de Montigny, C. *Nature* 312, 363–364 (1984).

Sheehan, D. V. *Drug Therapy* 12, 49 (1982).

Sheehan, D. V., Coleman, J. H., Greenblatt, D. J., Jones, K. J., Levine, & P. H. et al. *J. Clin. Psychopharmac.* 4, 66–75 (1984).

Chouinard, G., Annable, L., Fontaine, R. et al. *Psychopharmac.* 77, 229–233 (1982).

Woodruff, G. N., Hill, D. R., Boden, P., Pinnock, R., Singh, L. & Hughes, J. *Neuropeptides* 19, 45–56 (1991).

Dockray, G. J. *Br. Med. Bull.* 38, 253–258 (1982).

Passaro, E., Debas, H., Olandorf, W. & Yamada, Y. *Brain Res.* 241, 335–340 (1982).

Freeman, A. S. & Chiodoi, L. A. *Brain Res.* 439, 266–274 (1988).

Hamilton, M. *Br. J. Med. Psychol.* 32, 50 (1959).

Hamilton, M. *Br. J. Soc. Clin. Psychol.* 6, 278–296 (1967).

The structured clinical interview for DSM II (SCID-P) Feb. 1985 version. Spitzer, R., Williams, J. & Gibbons, M. Psychometrics Division, New York State Psychiatric Institute, New York (1985).

Beck, A. T., Ward, C. H., Mendelson, M., Mock, J. E. & Erbaugh, J. K. *Arch. Gen. Psychiatr.* 4, 561–571 (1961).

Singh, L., Field, M. J., Hughes, J., Menzies, R., Oles, R., Vass, C. A. & Woodruff, A. N. *Br. J. Pharmac.* 104, 239–245 (1991).

BLOOD LEVELS OF CCK PEPTIDES RELATIVE TO PANIC DISORDER TREATMENT

This is a continuation of application Ser. No. 08/168,913 filed on Dec. 16, 1993, now abandoned, which is a continuation of 07/914,849 which parent application was filed on Jul. 15, 1992, now abandoned.

TECHNICAL FIELD

The present invention relates to the relationship between cholecystokinin (CCK) and panic disorder. More specifically, the present invention provides 1) a method of treating a patient having a panic disorder, 2) a method of diagnosing panic disorder in a patient, 3) a method of determining the efficacy of a drug for the treatment of panic disorder, and 4) a method of predicting the vulnerability of a patient to panic disorder.

BACKGROUND OF THE INVENTION

The present invention relates to the relationship between panic disorder and cholecystokinin (CCK).

Panic disorder affects 3.6% of the general population(1) and 10–14% of patients in cardiology practices (2,3). It is a chronic relapsing illness(4,5) characterized by paroxysmal anxiety attacks that strike suddenly and for no apparent reason. Seventy-five percent of its victims are women(6). It has a unimodal age of onset (mean 23 years) rarely starting before age 12 or after age 45(7) and is 12 times more frequent in the 25–44 age group than in the 65+ age group(6). Panic disorder is more common in monozygotic than in dizygotic twins(8). Its inheritance pattern is consistent with single locus genetics (9,10,11) and preliminary evidence implicates the long arm of chromosome 16(12). It is associated with an increased risk of mitral valve prolapse(13), hypertension(14), alcohol abuse and dependence(15), and has an excess mortality from suicide and among men from cardiovascular death(16). The lack of understanding of the biochemical basis of panic disorder is hampering the development of drugs effective in the treatment of this disorder.

Recently Bradwejn, et al.(17) reported that intravenous administration of 25–50 micrograms of CCK-4 precipitated panic attacks at a greater rate in panic disorder victims than normal controls. Bradwejn and de Montigny(18) previously reported that CCK induced activation of hippocampal neurones can be antagonized by benzodiazepines. Since some CCK antagonists have a benzodiazepine structure(19) and panic disorder responds well to high potency benzodiazepines(20,21,22), their action on CCK might be the cause of their therapeutic effect.

Cholecystokinin (CCK), previously called pancreozymin, is a major gastrointestinal hormone(23). It is also one of the most common neuropeptides in the brain(24,25). CCK peptides exist in several molecular forms, the most abundant being the sulphated octapeptide CCK-8S (26). CCK containing neurones have a wide distribution in the brain(27). In certain neurones, CCK coexists with other putative neurotransmitters. So far two types of CCK receptors have been identified. The CCK-A (alimentary) receptor is located predominantly in peripheral tissues with minor distribution in discrete brain areas. The CCK-B (brain) receptor is widely distributed in the brain and has similarities to the peripheral gastrin receptor(28).

Although much attention has been focused on CCK, since it was localized in the brain over 15 years ago, its major functional role remains elusive(29). CCK peptides, when injected into the lateral ventricle of the rabbit(30), diffuse rapidly into the peripheral blood, suggesting the possibility that blood levels of CCK might reflect activity of central CCK neurones. Currently there is only indirect evidence to suggest that CCK-8S or CCK-4 might have access to the CNS(31,32).

The lack of specific and sensitive methods for measuring the various molecular forms of CCK peptides has hampered investigations on the biological role of CCK. Recently, the inventors of the present invention developed an HPLC method (U.S. patent application No. 712,664, filed Jun. 10, 1991 now abandoned) using electrochemical detection for simultaneously measuring multiple molecular forms of CCK in human brain and body fluids. Using the HPLC assay for CCK peptides, the present invention is derived from a comparison of the basal CCK levels and food induced changes in a group of panic disorder subjects and a group of normal controls. Also the effect of the most commonly used antipanic drugs on CCK peptide levels were examined.

Utilizing the above investigation, applicants further and most significantly characterized the relationship between CCK peptides and panic disorder to the extent that a method of treating a patient having a panic disorder has been derived. The present invention further provides a method of diagnosing panic disorder in patients, as well as a method of determining the efficacy of a drug for the treatment of panic disorder in patients. Finally, the present invention further provides a method of predicting the vulnerability of a patient to panic disorder.

SUMMARY OF THE INVENTION

In accordance with the present invention, there is provided a method of treating a patient having a panic disorder, the patient having an elevated CCK peptide plasma level, by lowering the plasma CCK peptide level of the patient.

The present invention further provides a method of diagnosing panic disorder in a patient by obtaining a plasma sample from the patient and detecting that the patient's plasma contains elevated CCK peptide levels.

The present invention further provides a method of determining the efficacy of a drug for the treatment of panic disorder by detecting the ability of the drug to lower elevated CCK peptide levels in a model for panic disorder.

Finally, the present invention further provides a method of dosing antipanic disorder drugs by monitoring the level of CCK peptide of the patient and detecting the lowering of the elevated level of the CCK peptide in the patient.

FIGURES AND THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
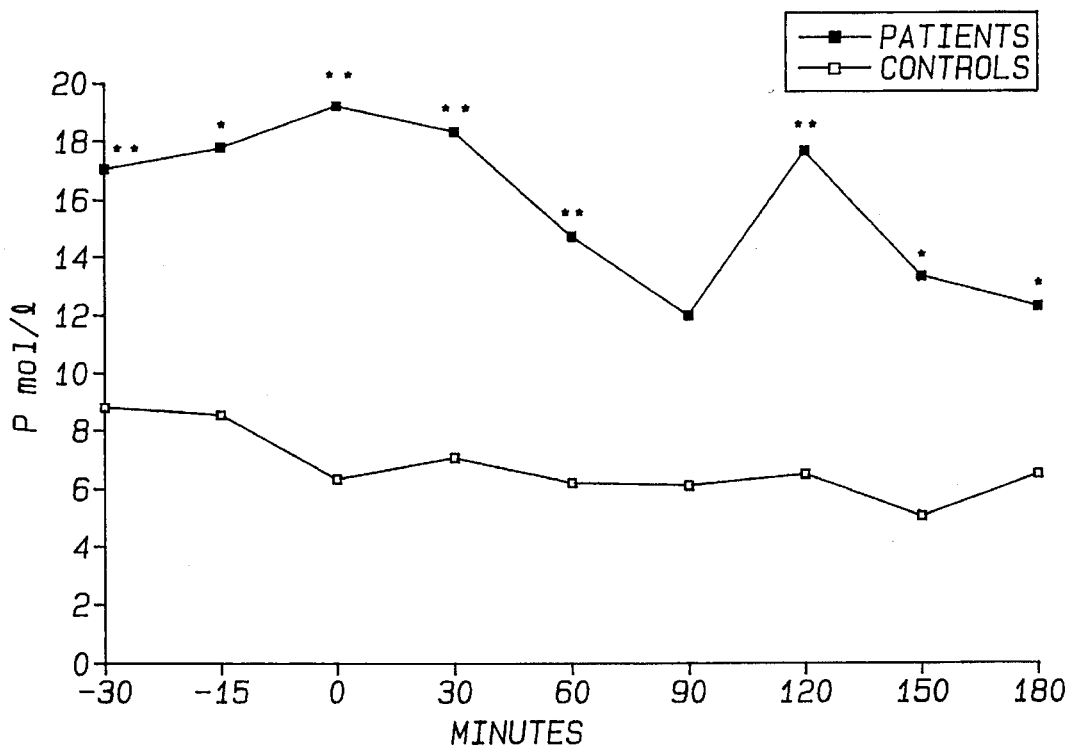
FIG. 1 shows mean levels of CCK-4 peptide in plasma (p mol/l) of patients(■) and controls (□) over time wherein the patient is challenged at 0 minutes and samples are taken every 30 minutes up to 180 minutes.

The present invention provides a characterization of the relationship between plasma levels of CCK peptides in patients having panic disorder disease versus controls. Based on the observations that an injection of synthetic CCK-4 can precipitate panic attacks, applicants previously suggested that the neuropeptide CCK may play a role in panic disorder. Combining this information, data was generated comparing basal levels of CCK-4 and CCK-8S and food induced changes in these peptides in panic disorder subjects and normal controls. Various useful clinical methods have been derived from this data which utilize the measurement of CCK peptide levels in the treatment of panic disorder, the development of drugs for panic disorder, and the dosing of such drugs for the treatment of panic disorder.

Several methods have been developed in accordance with the present invention. A first method provides a treatment of patients having a panic disorder, the patients having an elevated CCK peptide plasma level. Generally, the method is characterized by the step of lowering the plasma CCK peptide level of the patient. This can be accomplished by the administration of a therapeutic dose of a drug that lowers the elevated plasma CCK peptide level of the patient. Examples of drugs with such an effect have been found in the benzodiazepine class of drugs, nonbenzodiazepine anxiolytic drugs, and 5-HT uptake blockers. These drugs may be CCK peptide antagonists and inhibitors of CCK peptide synthesis. The drugs may significantly lower CCK-4 and/or CCK-8S levels. Specific examples of drugs are alprazolam, a triazols analog of 1,4 benzodiazepine (XANAX®), which is the only drug available for use in the United States for panic disorder, manufactured by Upjohn Pharmaceuticals, buspirone HCl (BuSpar®; a nonbenzodiazepine), manufactured by Bristol Myers, which is a drug used outside the United States for anxiety disorders and Prozac® (fluoxetine hydrochloride; a 5-HT uptake blocker), manufactured by Lily Pharmaceuticals.

The treatment would be accomplished by the administration of a pharmacologically-active dose of the drug which significantly lowered the elevated plasma CCK peptide level of the patient, as demonstrated by the experiments set forth below. For example, drugs such as alprazolam would be administered at a dose in the range of 0.25 mg to 4 mg per day, buspirone in a range of 15 mg to 60 mg per day and Prozac® in a range of 20 mg to 80 mg per day.

The present invention further provides a method of diagnosing panic disorder in a patient by obtaining plasma samples from the patient and detecting that the patient's plasma contains elevated CCK peptide levels. This can be accomplished by detecting elevated CCK-4 and/or CCK-8S levels. The following experimental data clearly demonstrates that CCK-4 levels greater than 11 p mol/l is a clear indication of panic disorder. The data shows that CCK-4 levels are much more greatly exaggerated and elevated in panic disorder patients than CCK-8S levels, although CCK-8S levels are consistently elevated albeit to a lesser degree.

Applicant has developed a method of testing patients by obtaining a baseline pretreatment blood sample. CCK peptide productions are stimulated in the patient, preferably by the administration of a meal. For the purposes of the experiments, patients were given a 600 caloric meal, as detailed below. However, other methods can be used to stimulate CCK production, such as amino acids, proteins, fats and oils, and carbohydrates.

CCK plasma levels are determined by the HPLC methods set forth in the aforementioned co-pending patent application. More specifically, the present invention further provides a method of determining the efficacy of a drug for the treatment of panic disorder. This is accomplished by detecting the ability of the drug to lower elevated CCK peptide levels in a model for panic disorder. Examples of human models for panic disorder are:

1. Injection of CCK4 or CCK8 peptides;
2. Infusion of Lactate; and
3. Inhalation of carbon dioxide.

The test is characterized by the step of detecting the ability of the drug to either antagonize CCK peptide activity or to block CCK peptide synthesis or decrease CCK release. Since models for subject activities can be tested in vitro or in vivo, a series of phase I and II tests can be accomplished.

The present invention further provides a clinical method for predicting the vulnerability of a patient to panic disorder. This is accomplished by obtaining a plasma sample from a patient and detecting whether the patient's plasma contains elevated CCK peptide levels. If the levels are determined to be elevated by the methods set forth above, then it can be concluded by the examining physician that the patient is highly susceptible to panic disorder. As discussed above, levels above those of age and sex-matched normal subjects are highly predictive of susceptibility to panic disorder.

Finally, the present invention provides a method of dosing a patient having elevated CCK peptide plasma levels with an antipanic disorder drug. Such dosing is critical in the clinic. Presently, there are reports of the difficulty of such dosing. The present invention is characterized by the steps of administering the drug to the patient and the monitoring of the lowering of the plasma CCK peptide levels of the patient. Once the peptide levels are lowered from the elevated levels to levels within the control range of age and sex-matched normal subjects, as set forth in the following experimental section, the physician can determine that a proper dosage of the drug has been administered.

The following experimentation provides evidence of the utility of the various inventive methods set forth above and provides detailed examples of preferred methods in accordance with the present invention.

METHODS

Subject Selection

Since panic disorder is three times more common in women than men, and pilot data suggest gender differences in CCK peptide levels, the study was limited to women. Because age may also influence CCK, the study stratified for age by choosing equal numbers of patients and controls from several age groups (i.e., aged 20–30, 30–40, 40–50 and 50–65 years). Panic disorder subjects had to meet DSM-III-R criteria for panic disorder. Controls could not be included if they had a current or past history of any psychiatric illness. Six panic disorder subjects were recruited from the anxiety disorders clinic of the University of South Florida Department of Psychiatry. Six normal controls were recruited through an advertisement in the media. All subjects signed a written informed consent, were given full psychiatric and medical evaluations, and underwent routine laboratory tests and a structured clinical interview for DSM-III-R (SCID-P)(33). Any subjects with abnormal blood values (CBC or SMA 25) were excluded. All subjects completed the protocol. However, one subject (aged 46) had to be eliminated from the analysis because of a contaminant in one of the reagents.

Procedures

Testing occurred between 7:00 a.m. and 11:00 a.m. to control for any circadian variations in CCK levels. After fasting overnight (12 hours) and abstaining from medication, alcohol, tobacco, coffee and caffienated drinks, subjects completed the baseline clinical scales and were then seated comfortably in a reclining position. An angiocatheter was placed in a vein in the antecubital fossa. Since food is a natural stimulus to CCK, a 600 calorie meal containing 34.5 g fat, 21.2 g protein and 51.1 g carbohydrate was provided. Blood was collected in tubes containing the protease inhibitors, aprotinin and bestatin, at −30, −15 and zero minutes before and at 30 minute intervals until 180 minutes after food ingestion. All samples were centrifuged. Plasma levels of CCK-8S sulphated and CCK-4 were determined by HPLC with electrochemical detection as set forth in detail in U.S. patent application Ser. No. 712,664, filed Jun. 10, 1991 now abandoned, which is incorporated herein by reference. Vital signs (blood pressure and heart rate) were monitored throughout the study. The Sheehan Patient Rated Anxiety Scale (SPRAS II) (Part II) (34), measuring current anxiety, was also administered following each blood collection.

To study the effect of commonly used antipanic drugs, subjects were pretreated orally with the appropriate compounds and the blood CCK levels were monitored as shown in the Figures.

RESULTS

Table 1 shows mean CCK-4 and Table 2 shows CCK-8S plasma levels for panic disorder subjects and normal controls over the testing period. Clinical data collected at baseline, immediately before testing, included a series of anxiety(34,35), panic(34), depression(36,37), phobia(34) and disability rating scales(34). Panic disorder subjects had a mean±s.d. duration of illness of 10.5±14.8 years, range 1–40 years, their means±s.d. number of panic attacks per week in the week prior to testing was 8.2±4.8. Symptom severity scores taken at baseline were higher in the panic disorder group compared to controls on all of the measures used and comparable to the scores of panic disorder subjects in previous studies(38).

Statistical Analyses

To control for possible age effects, two-way analyses of variance (ANOVA), with group (panic disorder vs normal controls) and age (<40 years vs 40+ years) as between group factors, were performed. Significance was stipulated at $P<0.05$, trends as $P>0.05<0.10$. All statistical tests were two tailed.

FIG. 1 shows plasma CCK-4 levels in patients before and after challenge by the 600 calorie meal. Significant group effects (designated as **) were evident at −30 ($P=0.05$), zero ($P=0.04$), 30 ($P=0.05$), 60 ($P=0.024$) and 120 ($P=0.015$) minutes with trends toward significance (designated as *) at −15 ($P=0.08$), 150 ($P=0.09$) and 180 ($P=0.06$) minutes. No significant age effects were found. Group x age interaction effects were significant at 60 ($P=0.05$) and 120 ($P=0.05$) minutes. As a group, panic disorder subjects consistently had higher CCK-4 levels than controls, with younger panic subjects, aged <40 years, showing three-fold higher CC-4 levels compared to controls in both age groups and two-fold higher levels compared to older (40+) panic subjects. This data records a basis for diagnosing panic disorder patients by detecting plasma CCK-4 levels of the patients.

Figure 2:
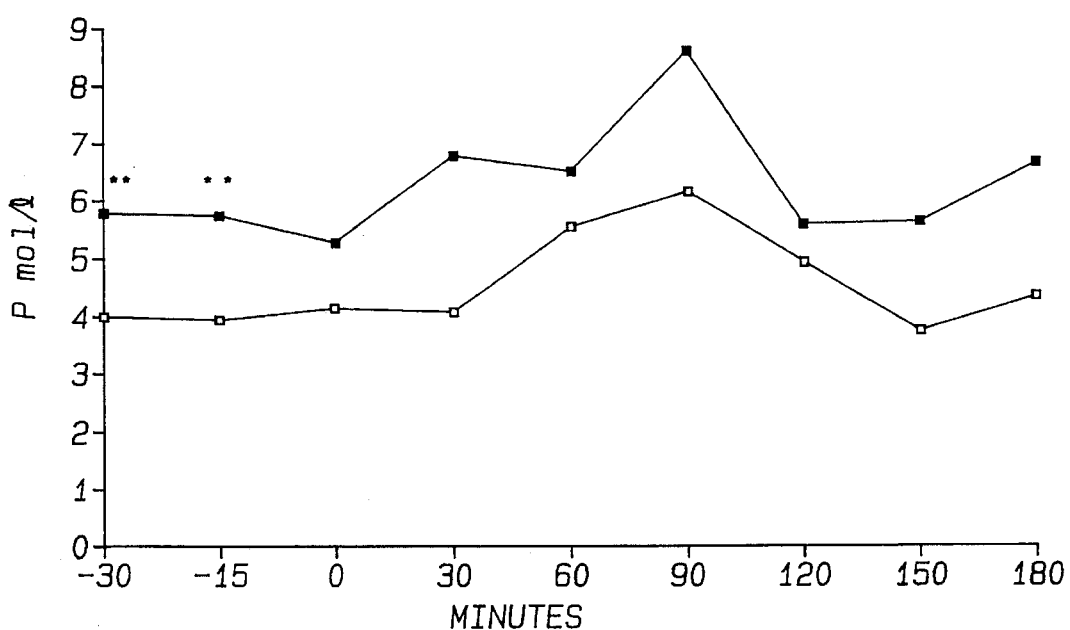
FIG. 2 shows CCK-MS levels in plasma (p mol/l) of patients (■) and controls (□) for 180 minutes after challenge.
Figure 3:
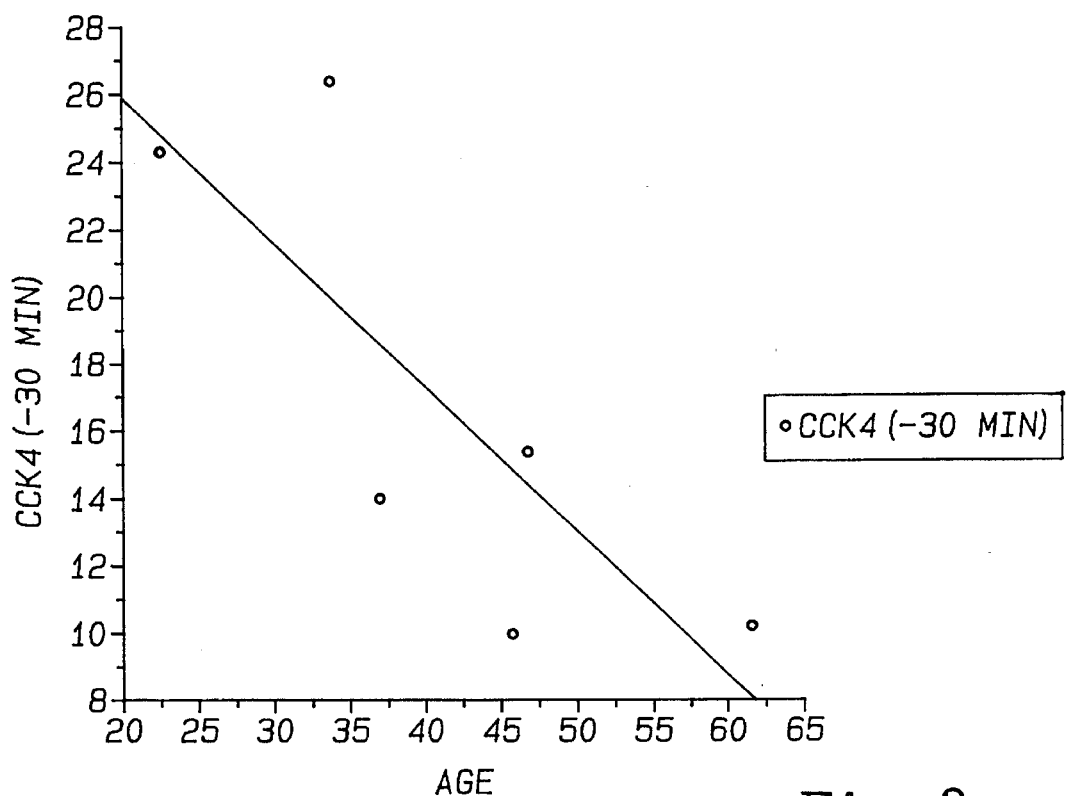
FIG. 3 shows the relationship between age and CCK-4 plasma levels in panic disorder patients.
Figure 4:
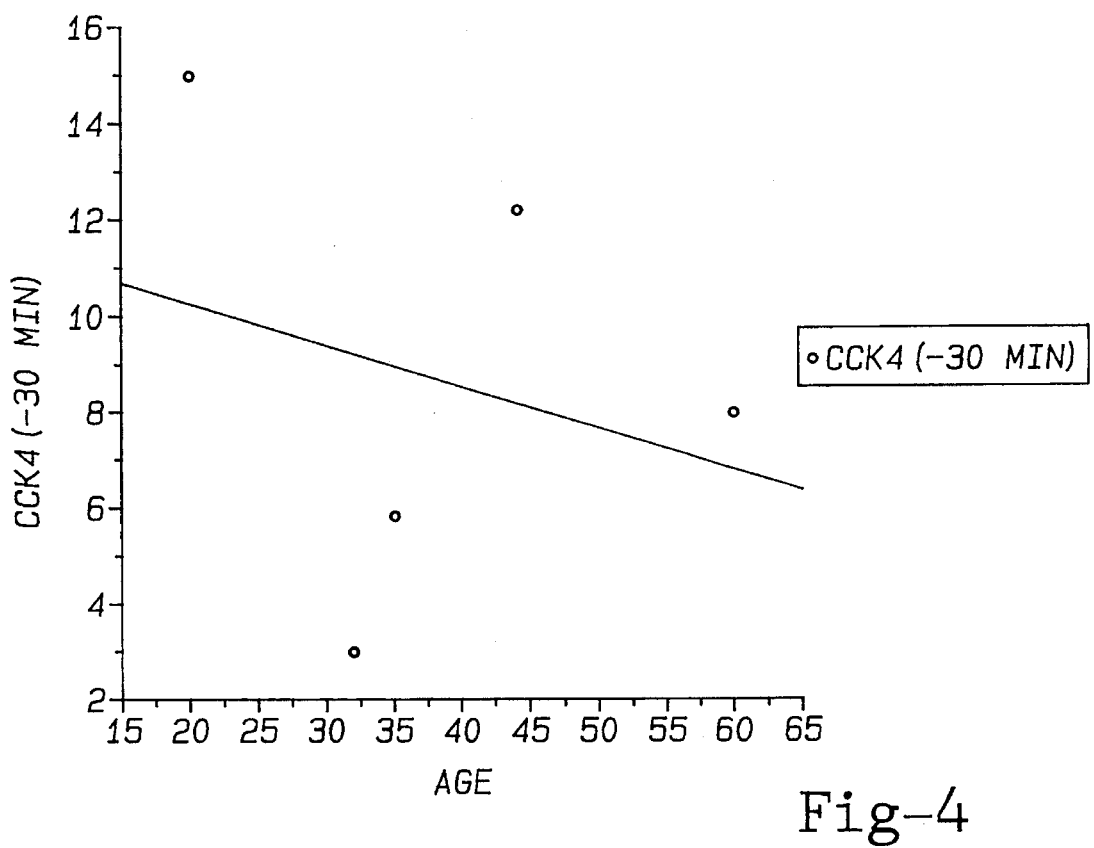
FIG. 4 is a graph showing the relationship between age and CCK-4 plasma levels in control subjects.
Figure 5:
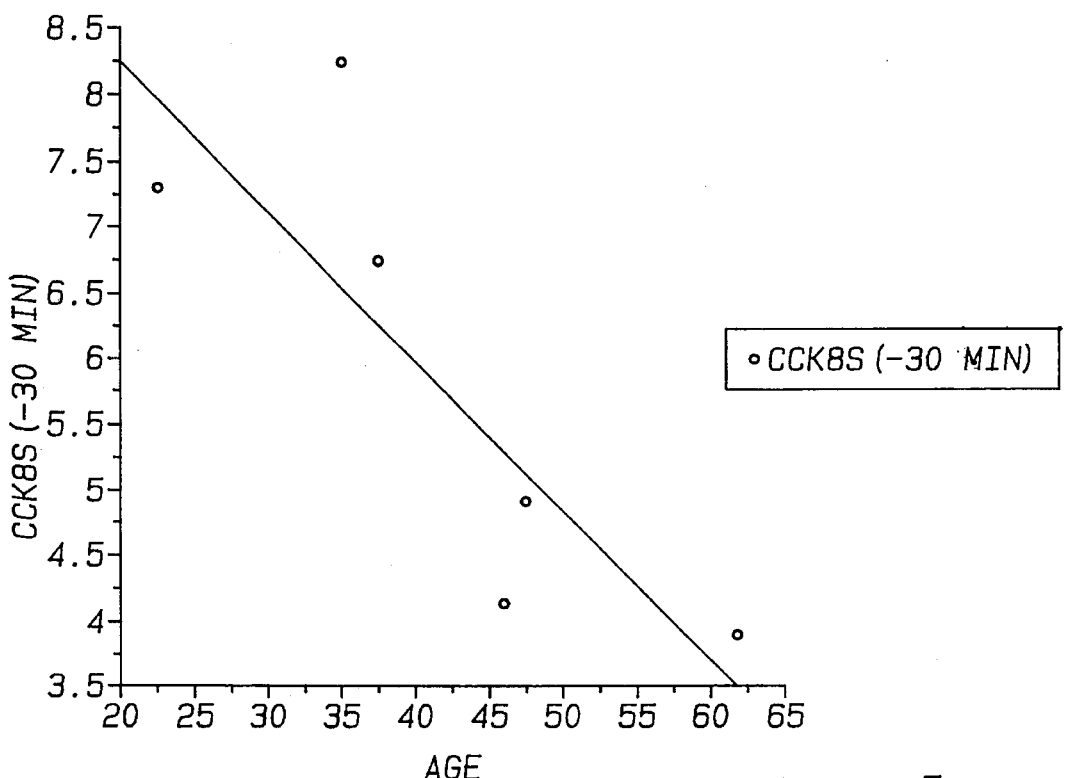
FIG. 5 is a graph showing the relationship between age and CCK-8S plasma levels in panic disorder patients.
Figure 6:
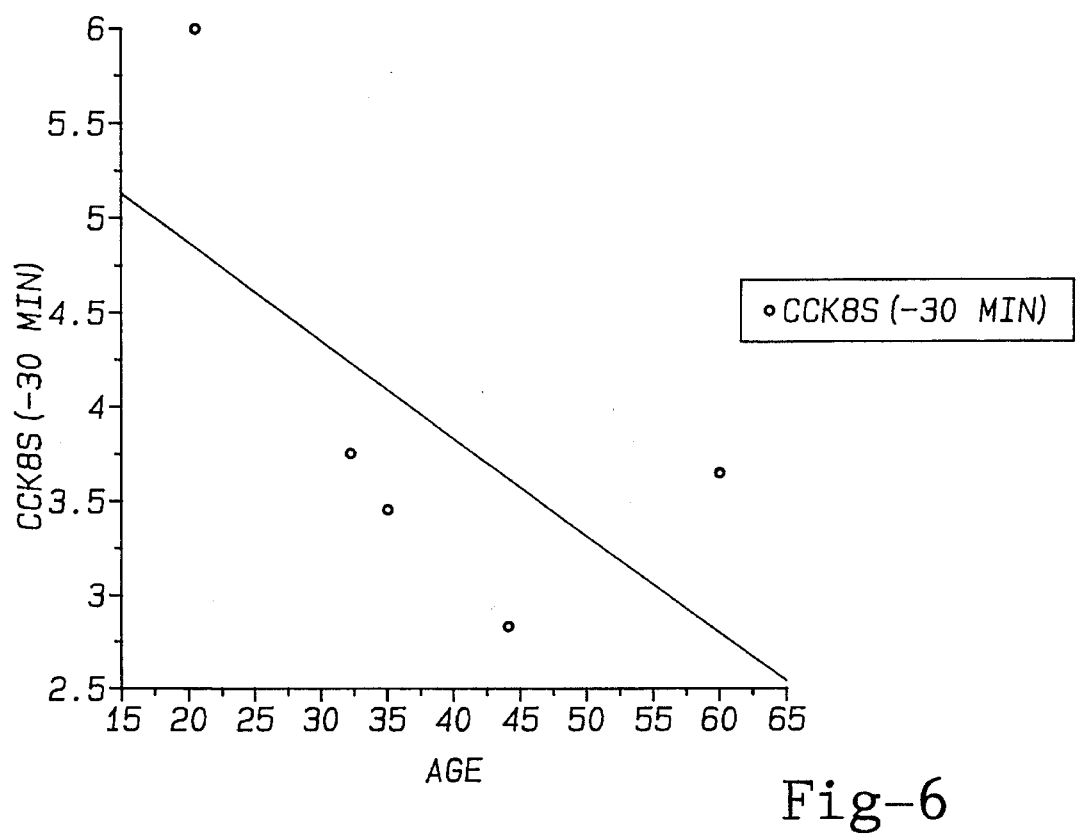
FIG. 6 is a graph showing the relationship between age and CCK-8S plasma levels in control subjects.

FIG. 2 shows plasma CCK-8S levels of patients before and after challenge. Significant group effects were observed for CCK-8S at −30 ($P=0.008$) and −15 ($P=0.01$) minutes with panic disorder subjects showing higher CCK-8S levels than controls at each of these time points. The between factor age was significant at −30 ($P=0.006$), −15 ($P=0.003$) and zero ($P=0.028$) minutes and showed trends towards significance ($P=0.09$) at 60 and 150 ($P=0.067$) minutes. A significant group by age interaction effect was observed at −15 minutes only ($P=0.04$). In general, younger subjects (panic disorder and controls) had 1.5 to 2 times higher CCK-8S levels at all time points than older subjects (FIGS. 3–6).

There was no evidence that CCK-4 or CCK-8S levels were differentially blunted or augmented by the food challenge. Group differences in average and maximum post challenge CCK-4 and CCK-8S levels were not significant when basal (mean prechallenge) values were controlled using analysis of covariance (ANCOVA). However, there was considerably more fluctuation in CCK-4 and CCK-8S levels in the panic disorder group compared to the control group (Table 2).

Panic disorder subjects showed a median of five (out of a possible eight) changes of 30% or more in CCK-4 levels between intervals and a median of three changes in CCK-8 levels between intervals. Comparable median numbers of changes for control subjects were 2 and 1 respectively.

Figure 7:
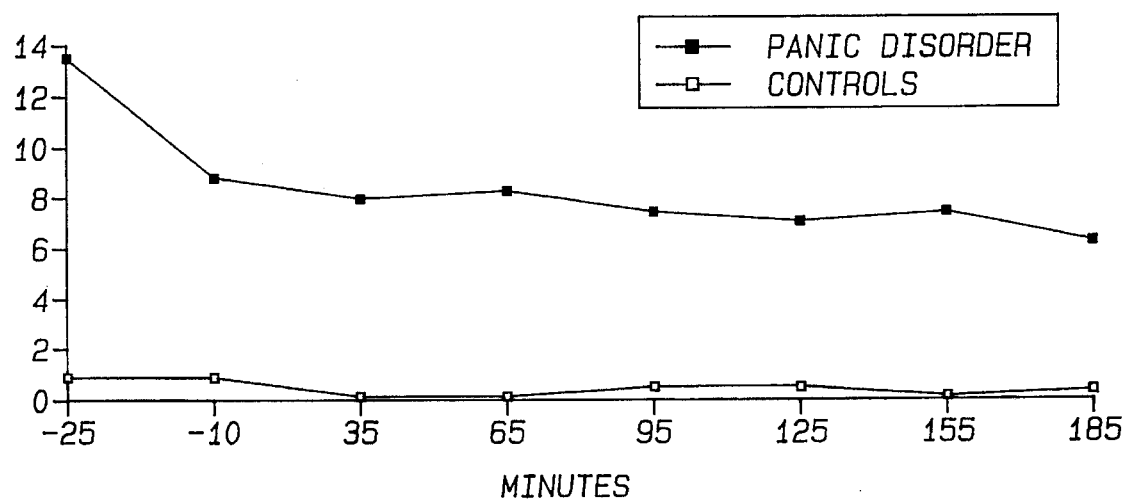
FIG. 7 is a Sheehan Patient Rated Anxiety Scale (Part II) graph comparing panic disorder patients (■) and controls (□)

There was no evidence among panic subjects of a relationship between basal CCK-4 or CCK-8S levels (expressed for each as the mean of the three pre-challenge time points) and duration of illness, previous medication treatment, or severity scores on any of the symptom severity scales taken at baseline (Table 3). Current anxiety symptom scores, as shown in FIG. 7, showed a significant decrease among panic subjects, from 13.2±11.9 at −25 minutes to 6.4±7.3 at 180 minutes ($P=0.001$, repeated measures ANOVA), with most of the reduction occurring in the first 30 minutes, before the food challenge. There was no evidence of an increase or decrease in anxiety among controls or of a relationship in either group between anxiety scores and CCK-4 or CCK-8S levels. Vital signs (blood pressure and pulse) were normal throughout testing. No relationship between vital signs and CCK-4 and CCK-8S levels was observed.

Figure 8:
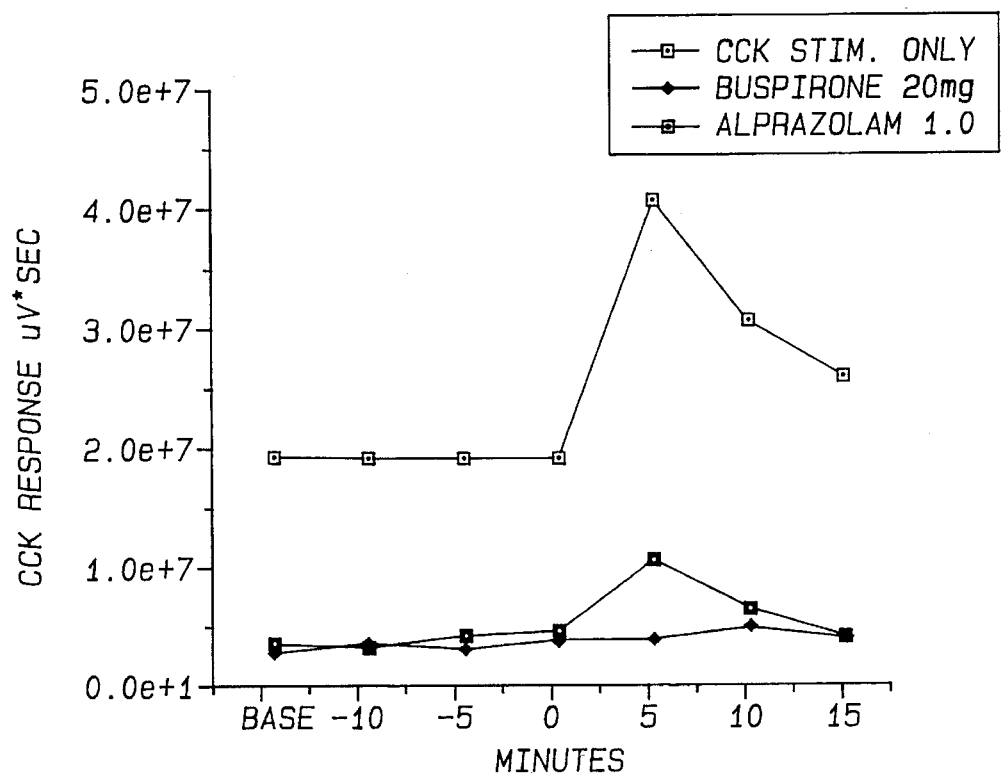
FIG. 8 is a graph showing the effect of anti-anxiety drugs on CCK plasma levels wherein (□) represents CCK stimulation of patients only, (♦) shows patients who were given buspirone (20 mg.) and (◻) represents patients given alprazolam (1 mg.).

FIG. 8 shows the effect of pretreating subjects with alprazolam or buspirone on the blood CCK level. Both of the drugs blunted the increase in CCK levels. This is critical evidence of the relationship between CCK peptides and the cause of panic disorder, as well as showing the relationship between antipanic drugs and CCK peptide levels. Accordingly, CCK peptide levels can be used to dose antipanic drugs. Further, CCK peptides can be used as a marker for disorder disease and the susceptibility of patients to disorder syndromes.

The experimental results show a significant baseline elevation of CCK-8S levels and an even more pronounced elevation of CCK-4 levels in panic disorder subjects compared to normal controls even in the small sample examined in this study, as shown in FIGS. 1 and 2. This is of interest because the smaller peptide CCK-4 might have a better chance to cross the blood brain barrier, although this has not yet been documented. The relationship between plasma levels of CCK and brain or CSF levels of CCK remains unknown. Increased peripheral plasma levels of CCK may have a role in the many peripheral symptoms associated with panic disorder. It is not known whether these elevated CCK peptide levels are of central or peripheral origin, or both. Whether the target of action in panic disorder patients is central or peripheral also remains to be resolved.

CCK peptide levels fluctuated more frequently in panic disorder subjects than normal controls. The levels of CCK-4 in normal subjects seems to be regulated within a narrow range. In contrast, the levels of CCK-4 in panic disorder subjects show frequent fluctuations which may reflect a disrupted regulation of CCK homeostasis.

There was a significant relationship between CCK peptide levels and age. Younger panic disorder subjects (<40 years) showed a three-fold higher CCK level compared to controls and a two-fold higher level compared to older panic disorder subject (>40 years). This finding is of interest since panic disorder is largely an illness of women during their childbearing years, has means age of onset in the early twenties(7), and is 12 times more frequent in the 25–44 age group than in the 65+ age group(6).

The panic disorder subjects had higher CCK peptide levels and higher scores on all of the anxiety, phobia, disability, depression and panic psychometric measures. However, within each group (panic disorder and controls), there was no evidence of a relationship between anxiety scores and CCK-4 or CCK-8S levels. No relationship was found between CCK peptide levels and nausea, suicidal ideation, heart rate, blood pressure, duration of panic disorder, previous medication treatment or severity scores on any of the symptom severity scales at baseline.

It was found that alprazolam, the only approved antipanic agent in the United States, lowered the blood level of CCK. Also buspirone, a drug widely used in the treatment of anxiety disorders, also was very effective in lowering the CCK level. Thus, the lowering of CCK levels is an important function of these antianxiety drugs. Specific drugs that lower CCK levels might prove to be more effective in the treatment of anxiety disorders than currently available drugs.

Hence, the experimental data shows elevated CCK-4 and CCK-8S plasma levels in panic disorder subjects when compared with normal controls. Younger panic disorder subjects had higher basal levels of CCK peptides. These findings show that CCK levels are a marker of panic disorder and are the basis for a diagnostic test for panic disorder as well as a marker of treatment response. Given the findings that CCK-B antagonists have antianxiety effects in animal models(39), it is possible that CCK antagonists can be effective novel agents in the treatment of panic disorder. The ability of antianxiety drugs to lower CCK levels in humans as shown herein also supports this view.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

TABLE 1

| | PLASMA CCK8S LEVELS | | | | | | | | |
|---|---|---|---|---|---|---|---|---|---|
| | TIME (MIN) | | | | | | | | |
| | −30 | −15 | 0 | 30 | 60 | 90 | 120 | 150 | 180 |
| PATIENTS | | | | | | | | | |
| 1 | 3.84 | 3.86 | 3.72 | 3.54 | 3.15 | 14.79 | 1.25 | 1.82 | 2.85 |
| 2 | 4.05 | 3.01 | 3.38 | 6.51 | 4.37 | 4.06 | 5.99 | 4.48 | 6.89 |
| 3 | 4.96 | 4.07 | 3.98 | 5.09 | 5.08 | 4.96 | 7.62 | 3.85 | 5.02 |
| 4 | 6.73 | 8.60 | 5.19 | 4.26 | 6.93 | 9.15 | 3.34 | 5.93 | 7.74 |
| 5 | 7.31 | 7.62 | 7.42 | 12.25 | 8.67 | 10.08 | 8.42 | 9.69 | 7.78 |
| 7 | 8.14 | 7.41 | 8.22 | 8.93 | 10.56 | 9.69 | 5.90 | 6.75 | 7.88 |
| CONTROLS | | | | | | | | | |
| 8 | 5.93 | 6.16 | 5.98 | 6.10 | 12.45 | 14.22 | 10.74 | 6.24 | 6.43 |
| 9 | 2.85 | 2.87 | 2.91 | 3.17 | 3.19 | 5.58 | 2.91 | 2.99 | 2.97 |
| 10 | 3.69 | 3.37 | 4.33 | 4.11 | 5.18 | 4.94 | 3.97 | 3.79 | 7.03 |
| 11 | 3.79 | 3.20 | 3.66 | 3.03 | 3.69 | 3.22 | 3.09 | 2.35 | 2.85 |
| 12 | 3.48 | 3.44 | 3.53 | 3.90 | 3.62 | 3.65 | 3.40 | 3.00 | 3.04 |
| Means: Patients vs Controls | | | | | | | | | |
| patients | 5.84 | 5.76 | 5.32 | 6.76 | 6.46 | 8.79 | 5.42 | 5.42 | 6.36 |
| controls | 3.95 | 3.81 | 4.08 | 4.06 | 5.62 | 6.32 | 4.82 | 3.67 | 4.46 |

TABLE 2

PLASMA CCK4 LEVELS

| | TIME (MIN) | | | | | | | | |
|---|---|---|---|---|---|---|---|---|---|
| | −30 | −15 | 0 | 30 | 60 | 90 | 120 | 150 | 180 |
| PATIENTS | | | | | | | | | |
| 1 | 10.25 | 9.97 | 7.76 | 13.41 | 5.80 | 14.91 | 8.85 | 11.42 | 13.24 |
| 2 | 9.96 | 9.22 | 9.81 | 12.14 | 8.70 | 4.56 | 10.99 | 4.41 | 12.77 |
| 3 | 15.55 | 11.34 | 18.67 | 12.80 | 12.26 | 5.25 | 11.77 | 11.58 | 8.81 |
| 4 | 14.06 | 12.61 | 12.25 | 6.75 | 14.65 | 9.51 | 35.26 | 5.44 | 6.70 |
| 5 | 24.69 | 28.70 | 25.83 | 30.81 | 17.60 | 14.59 | 17.48 | 18.22 | 14.56 |
| 7 | 26.45 | 30.66 | 40.70 | 34.51 | 28.90 | 22.15 | 19.87 | 29.44 | 20.05 |
| CONTROLS | | | | | | | | | |
| 8 | 14.93 | 16.38 | 9.17 | 9.33 | 8.84 | 9.74 | 8.84 | 8.44 | 8.51 |
| 9 | 12.42 | 12.34 | 7.66 | 6.60 | 6.15 | 5.34 | 8.02 | 4.84 | 6.94 |
| 10 | 7.43 | 7.69 | 7.98 | 7.71 | 8.78 | 8.73 | 7.60 | 5.56 | 10.14 |
| 11 | 3.13 | 2.79 | 2.12 | 7.64 | 3.41 | 3.68 | 4.64 | 3.51 | 4.12 |
| 12 | 5.92 | 4.06 | 3.88 | 4.40 | 3.69 | 2.99 | 4.08 | 3.45 | 3.66 |
| Means: Patients vs Controls | | | | | | | | | |
| patients | 18.02 | 18.67 | 19.04 | 16.80 | 14.73 | 11.10 | 16.87 | 12.99 | 11.72 |
| controls | 5.49 | 4.84 | 4.66 | 6.58 | 5.29 | 5.13 | 5.44 | 4.17 | 6.22 |

TABLE 3

| Total # of changes of 30% or more between intervals | | |
|---|---|---|
| | CCK-8S | CCK-4 |
| PT ID | | |
| 1 | 4 | 6 |
| 2 | 4 | 5 |
| 3 | 3 | 5 |
| 4 | 6 | 6 |
| 5 | 2 | 2 |
| 7 | 1 | 4 |
| 8 | 2 | 2 |
| 9 | 2 | 5 |
| 10 | 1 | 1 |
| 11 | 0 | 2 |
| 12 | 0 | 3 |
| mean/pts | 3.3 | 4.7 |
| st dev/pts | 1.8 | 1.5 |
| median/pts | 3.5 | 5 |
| mean/controls | 1 | 2.6 |
| st dev/controls | 1 | 1.5 |
| median/control | 1 | 2 |

TABLE 4

Clinical conditions of panic disorder subjects and controls at baseline

| | Sex | Age/yrs | Dur/illness/ yrs # | Panic Attacks | Ham-A | SCRAS | SPRAS | Ham-D | Agoraphob/ Fear |
|---|---|---|---|---|---|---|---|---|---|
| Pain Disorder | F | 22 | 1 | 7 | 30 | 51 | 69 | 21 | 42 |
| Subjects (n = 6) | F | 34 | 2 | 8 | 9 | 26 | 43 | 7 | 16 |
| | F | 37 | 10 | 1 | 10 | 15 | 29 | 12 | 9 |
| | F | 46 | 40 | 8 | 9 | 34 | 17 | 10 | 9 |
| | F | 47 | 4 | 9 | 24 | 42 | 70 | 16 | 7 |
| | F | 61 | 6 | 16 | 19 | 57 | 56 | 21 | 33 |
| Mean ± S.D. | | 41.2 ± 13.3 | 10.5 ± 14.8 | 8.2 ± 4.8 | 16.8 ± 8.9 | 37.5 ± 15.7 | 47.3 ± 21.6 | 14.5 ± 5.8 | 19.3 ± 14.7 |
| Controls (n = 5) | F | 20 | | 0 | 0 | 1 | 2 | 4 | 0 |
| | F | 32 | | 0 | 2 | 1 | 1 | 2 | 2 |
| | F | 35 | | 0 | 0 | 0 | 0 | 2 | 0 |
| | F | 44 | | 0 | 4 | 1 | 0 | 1 | 0 |
| | F | 60 | | 0 | 3 | 2 | 9 | 3 | 1 |
| Mean ± S.D. | | 38.2 ± 14.9 | | 0 | 1.8 ± 1.8 | 1.0 ± .7 | 2.4 ± 3.8 | 2.4 ± 1.1 | .6 ± .9 |

REFERENCES

1. Klerman, G. L., Weissman, M. M., Ouellette, R., Johnson, J. & Greenwald, S. *JAMA* 256, 742–746 (1991).
2. White, P. D. & Jones, T. D. *New Eng. Am. Heart J.* 3, 302–318 (1928).
3. Wood, P. *Br. Med. J.* 1, 767–772, 805–822, 845–851 (1941).
4. Wheeler, E. O., White, P. D., Reed, E. W., & Cohen, M. E. *JAMA* 142, 878–889 (1950).
5. Marks, I. & Lader, M. *J. Nerv. Ment. Dis.* 156, 3–18 (1973).
6. Robins, L. N. Helzer, J. E., Weissman, M. M. et al. *Arch. Gen. Psychiatr.* 41, 949–958 (1984).
7. Sheehan, D. V., Sheehan, K. E., & Minichello, W. E. *Compr. Psychiatr.* 22, 544–553 (1981).
8. Torgersen, S. *Arch. Gen. Psychiatr.* 40, 1085–1089 (1983).
9. McNair, D. M. Kahn, R. J. in *Anxiety: New Research and Changing Concepts* (eds. Klein, D. F. & Rabkin, J.) 69–79 (Raven, New York 1981).
10. Crowe, R. R., Pauls, D. L. Slymen, D. J., & Noyes, R. *Am. J. Hum. Genetics* 32, 639–644 (1980).
11. Pauls, D. L., Bocher, K. D., Crowe, R. R. et al. *Am. J. Hum. Genet.* 32, 639–644 (1980).
12. Crowe, R. R., Noyes, R., Wilson, A. F. et al. *Arch. Gen. Psychiatr.* 44, 933–937 (1987).
13. Liberthson, R., Sheehan, D. V., King, M. E. et al. *Am. J. Psychiatr.* 143, 511–515 (1986).
14. Noyes, R., Clancy, J., Hoenk, P. R., & Slymen, D. J. *Comp. Psychiatr.* 19, 407–413 (1978).
15. Bibb, J. L. & Chambless, D. L. *Behav. Res. & Therapy* 24, 49–58 (1986).
16. Coryell, W., Noyes, R., & Clancy, J. *Arch. Gen. Psychiatr.* 39, 701–703 (1982).
17. Bradwejn, J., Koszycki, B. & Shriqui, C. *Arch. Gen. Psychiatr.* 48, 603–610 (1991).
18. Bradwejn, J. & de Montigny, C. *Nature* 312, 363–364 (1984).
19. Woodruff, A. N. & Hughes, J. *Ann. Rev. Pharm. Toxicol.* 31, 469–501 (1991).
20. Sheehan, D. V. *Drug Therapy* 12, 49 (1982).
21. Sheehan, D. V., Coleman, J. H., Greenblatt, D. J., Jones, K. J., Levine, P. H. et al. *J. Clin. Psychopharmac.* 4, 66–75 (1984).
22. Chouinard, G., Annable, L., Fontaine, R. et al. *Psychopharmac.* 77, 229–233 (1982).
23. Ivy, A. C. & Goldberg, E. *Am. J. Physiol.* 86, 599–613 (1928).
24. Vanderhaeghen, J. J., Signeau, J. E. & Gepts, W. *Nature* 257, 604–605 (1975).
25. Dockray, G. J. *Nature* 264, 568–570 (1976).
26. Rehfield, J. F. in *Gut Hormones* (ed Bloom, S. R.) 213–218 (Churchill Livingstone, Edinburgh, 1978).
27. Beinfield, M. C. *Neuropeptides* 3, 411–427 (1983).
28. Woodruff, G. N., Hill, D. R., Boden, P., Pinnock, R., Singh, L. & Hughes, J. *Neuropeptides* 19, 45–56 (1991).
29. Dockray, G. J. *Br. Med. Bull.* 38, 253–258 (1982).
30. Passaro, E., Debas, H., Olandorf, W. & Yamada, Y. *Brain Res.* 241, 335–340 (1982).
31. Cohen, S. L., Knight, M., Tamminga, C. A. & Chase, T. N. *Eur. J. Pharmac.* 83, 213–219 (1982).
32. Friedman, A. S. & Chiodoi, L. A. *Brain Res.* 439, 266–274 (1988).
33. Sheehan, D. V. *The Anxiety Disease* (Bantam Books, New York, rev. paperback ed., 1986).
34. Hamilton, M. *Br. J. Med. Psychol.* 32, 50 (1959).
35. Hamilton, M. *Br. J. Soc. Clin. Psychol.* 6, 278–296 (1967).
36. The structured clinical interview for DSM II (SCID-P) 2/85 version. Spitzer, R., Williams, J. & Gibbons, M. Psychometrics Division, New York State Psychiatric Institute, New York (1985).
37. Beck, A. T., Ward, C. H., Mendelson, M., Mock, J. E. & Erbaugh, J. K. *Arch. Gen. Psychiatr.* 4, 561–571 (1961).
38. Sheehan, D. V., Raj, B. A., Sheehan, K. H. & Soto, S. *Clin. Psychopharmac.* 10, 3–11 (1990).
39. Singh, L., Field, M. J., Hughes, J., Menzies, R., Oles, R., Vass, C. A. & Woodruff, A. N. *Br. J. Pharmac.* 104, 239–245 (1991).

What is claimed is:

1. A method of determining the efficacy of an anxiolytic drug for the treatment of panic disorders by administering the anxiolytic drug and detecting whether the the drug lowers elevated CCK peptide levels to the corresponding levels found in age- and sex-matched normal controls in a suitable model for panic disorders by analyzing blood plasma samples.

2. The method of claim 1 further detecting the ability of the drug to antagonize CCK peptide activity.

3. The method of claim 1 further detecting the ability of the drug to block CCK peptide synthesis.

4. The method of claim 1 wherein the model includes a human model of panic disorders selected from the group consisting of injection of CCK 4 or CCK 8 peptides, infusion of lactate, and inhalation of carbon dioxide.

5. The method of claim 1 wherein the model includes an animal model of panic disorder.

6. A method of dosing a patient having elevated CCK peptide plasma levels with an anxiolytic drug by
   administering the drug to a patient and
   monitoring blood samples taken from the patient in order to access the lowering of the elevated plasma CCK peptide levels of the patient to the corresponding levels found in age-and sex-matched normal controls.

7. The method according to claim 1 or 6 wherein said administering step includes administering 0.25 to 2.0 mg doses orally of the anxiolytic drug.

8. The method according to claim 1 or 6 wherein said detecting step further includes taking blood samples at 30 minutes, 60 minutes and 120 minutes after the administration of the anxiolytic drug.

9. A method of predicting the vulnerability of a patient to panic disorder by obtaining a plasma sample from the patient and detecting that the patient's plasma attains elevated CCK peptide levels greater than that of age and sex-matched normal subject by analyzing blood samples.

* * * * *